United States Patent
Mistry et al.

(10) Patent No.: US 7,440,939 B2
(45) Date of Patent: Oct. 21, 2008

(54) SYSTEM AND METHOD FOR INTER-RELATING MULTIPLE DATA TYPES RELATING TO PHARMACEUTICAL PRODUCTS, THERAPIES AND COMPANIES

(75) Inventors: Bop Mistry, Edgware (GB); Simon Thompson, Horsham (GB)

(73) Assignee: IMS Software Services Ltd., Plymouth Meeting, PA (US)

( * ) Notice: Subject to any disclaimer, the term of this patent is extended or adjusted under 35 U.S.C. 154(b) by 0 days.

(21) Appl. No.: 11/436,782

(22) Filed: May 18, 2006

(65) Prior Publication Data
US 2007/0022140 A1  Jan. 25, 2007

Related U.S. Application Data

(63) Continuation of application No. PCT/US2004/001476, filed on Jan. 20, 2004.

(51) Int. Cl.
G06F 17/30 (2006.01)
G07G 1/00 (2006.01)

(52) U.S. Cl. .............................. 707/3; 707/1; 707/100; 705/10

(58) Field of Classification Search ............... 705/1, 705/2–4, 10; 707/1–5, 100
See application file for complete search history.

(56) References Cited

U.S. PATENT DOCUMENTS

| | | | | |
|---|---|---|---|---|
| 5,961,151 A * | 10/1999 | Tung et al. | ................... | 283/56 |
| 6,055,507 A | 4/2000 | Cunningham | | |
| 6,243,615 B1 | 6/2001 | Neway et al. | | |
| 6,438,451 B1 | 8/2002 | Lion | | |
| 2003/0060483 A1* | 3/2003 | Day | ................... | 514/310 |
| 2004/0236630 A1* | 11/2004 | Kost et al. | ................... | 705/14 |
| 2005/0108044 A1* | 5/2005 | Koster | ................... | 705/2 |

* cited by examiner

Primary Examiner—Cheryl Lewis
(74) Attorney, Agent, or Firm—Baker Botts L.L.P.

(57) ABSTRACT

Techniques for inter-relating various types of data from a plurality of dissimilar data sources relating to marketed pharmaceutical products are disclosed. Various data types may be inter-related based on one or more common data features and displayed in a comprehensive format.

21 Claims, 12 Drawing Sheets

SYSTEM AND METHOD FOR INTER-RELATING MULTIPLE DATA TYPES RELATING TO PHARMACEUTICAL PRODUCTS, THERAPIES AND COMPANIES

CROSS-REFERENCE TO RELATED APPLICATIONS

This application is a continuation of International Application Serial No. PCT/US04/001476, filed Jan. 20, 2004, published Sep. 4, 2005, which is incorporated by reference in its entirety herein, and from which priority is claimed.

BACKGROUND OF INVENTION

1. Field of Invention

The present invention is directed to techniques for inter-relating multiple data types from a number of dissimilar data sources, and more particularly, techniques for creating a comprehensive data output from such interrelated data.

2. Description of Related Art

The pharmaceutical industry is one of the largest data generating industries in the world. Numerous manufacturers, suppliers, retailers, physicians and marketing firms generate vast amounts of information concerning, e.g., the use, benefits, and effects of a multitude of different pharmaceutical products. As a result, enormous amounts of differing types of data are often analyzed and passed to and from a variety of computer systems relating to the marketed pharmaceutical products.

Such data ranges from the types of products, therapies, and companies being marketed to the international classification of certain pharmaceutical products. Often, voluminous information is stored on a particular computer system or network without the ability to relate different types of data with other data. This problem is further exasperated by the fact that a number of pharmaceutical companies often produce the same or equivalent type of pharmaceutical product in numerous product categories.

Against this background, it has become increasing important to develop techniques that can inter-relate different types of data which relate to a marketed pharmaceutical product in order to acquire an accurate depiction of the worldwide, or regional, pharmaceutical market.

Accordingly, a need exists for a technique for providing a comprehensive data output utilizing all the various types of received data relating to one or more marketed pharmaceutical products.

SUMMARY OF THE INVENTION

An object of the present invention is to provide a technique for inter-relating various types of data from a plurality of dissimilar data sources.

Another object of the present invention is to provide a technique for inter-relating different types of information, which relate to marketed pharmaceutical products.

It is further an object of the present invention to provide such inter-related data in a human readable output.

In order to achieve these objectives, as well as others that will become apparent in the disclosure below, the present invention provides systems and methods for inter-relating a plurality of data types relating to marketed pharmaceutical products. In an exemplary method, product attribute information for two or more attributes that relate to the marketed pharmaceutical product are stored, a request for product attribute information concerning the marketed pharmaceutical product is received; and product attribute information items from the stored product attribute information are inter-related to the marketed pharmaceutical product in accordance with the request.

In a preferred embodiment, the inter-related data may be displayed to a user. Advantageously, the data may include product molecule data, physical dollar sales data, marketed pharmaceutical product relationship data, marketed pharmaceutical product anatomical therapy classification data, research and development product data, marketing data or pharmaceutical product companies data.

The inter-relation process may use any such data as the basis for inter-relation, or more than one type of data. In this way, a worldwide marketing and technical summary can be presented for pharmaceutical products, therapies, and/or companies with a query as minimal as simply querying by marketed product.

BRIEF DESCRIPTION OF THE DRAWINGS

For a more complete understanding of the present invention and the advantages thereof, reference may be made to the following description of an exemplary embodiment thereof, taken in conjunction with the accompanying drawings, in which.

Throughout the figures, the same reference numerals and characters, unless otherwise stated, are used to denote like features, elements, components or portions of the illustrated embodiments. Moreover, while the present invention will now be described in detail with reference to the figures, it is done so in connection with the illustrative embodiments

DETAILED DESCRIPTION OF THE PREFERRED EMBODIMENTS

The present invention provides techniques for inter-relating various types of data which may all relate, in some form, to a marketed product.

Figure 1A:
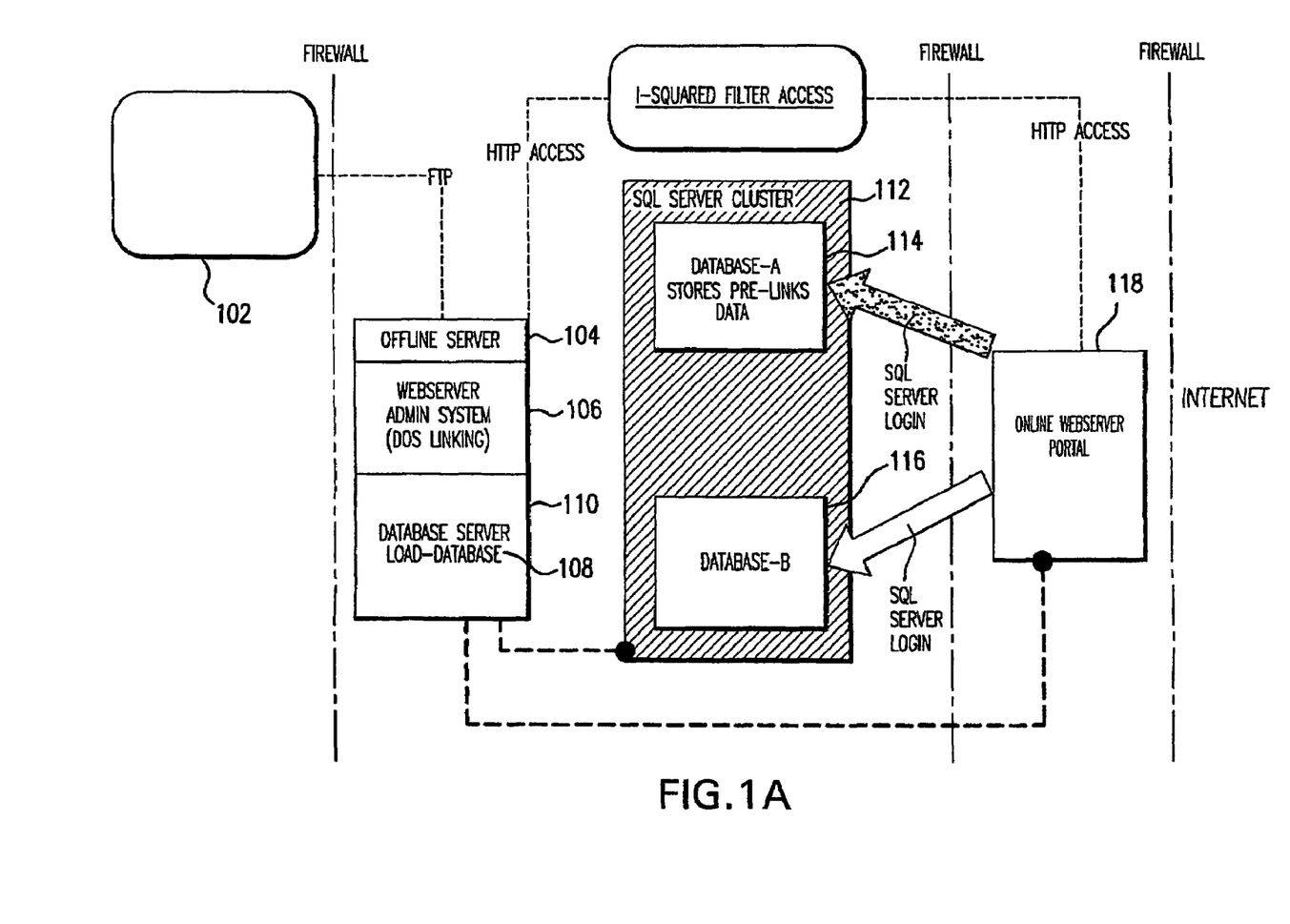
FIG. 1a is a illustrative diagram of an exemplary system in accordance with the present invention.

FIG. 1A depicts a first exemplary embodiment of a system according to the present invention. An IMS user 102 may copy load data files to an offline server 104 via FIT from within a firewall. A WebServer 106 that performs linking may be in communication with the Offline Server 104. The WebServer 106 and a portal on the offline server 104 may communicate with a load database 108 on the database server 110.

As part of a database switching process, the load database 108 may be backed up and may be copied onto a Server Cluster 112 so that it can be restored into a live database, such as Database A 114 or Database B 116, on the Server Cluster 112. Further, an Admin web application on the Offline Server 104 may copy and touch a configuration file on an Online Server. Thus, the prelinked data may be sent to the SQL server cluster 112.

A user may access the system over the internet, to seek product information, via an online WebServer portal 118, which communicates with the Server Cluster 112.

Figure 1B:
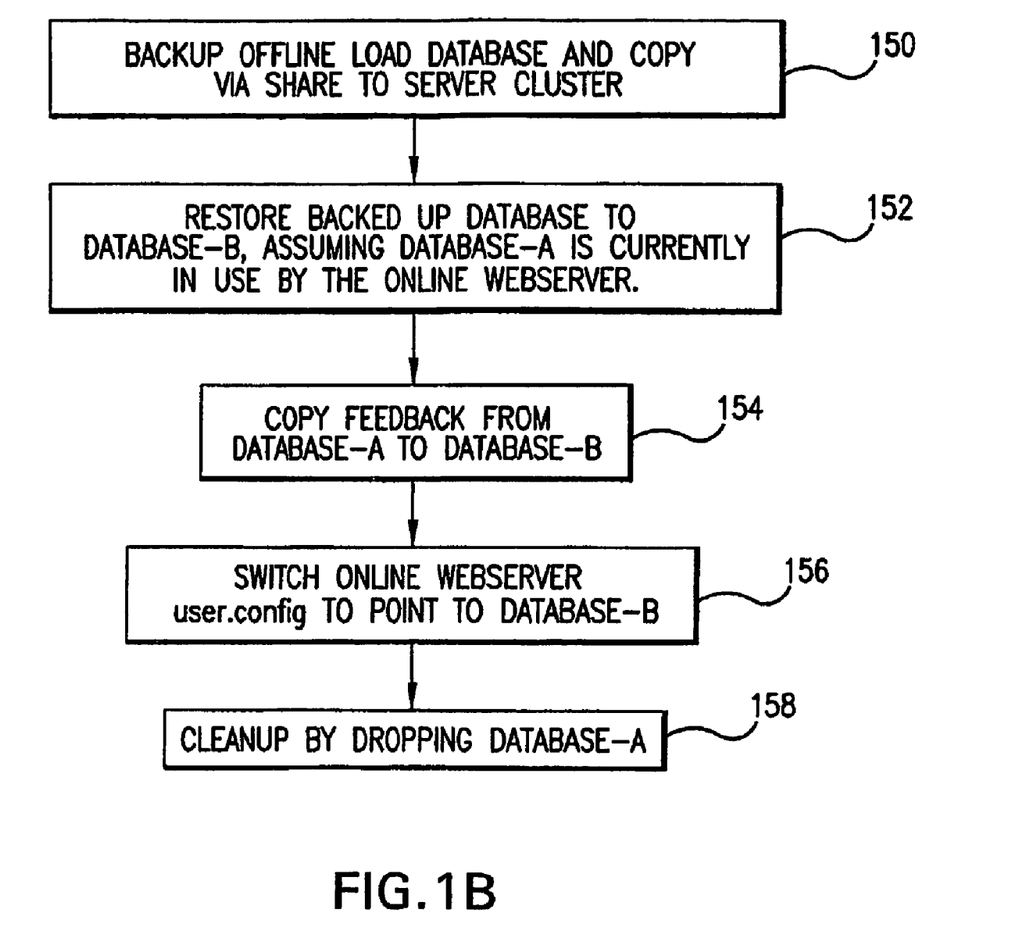
FIG. 1b is a flow diagram of an exemplary method in accordance with present invention.

In an exemplary procedure for database switching according to the present invention, the Offline Load Database may be backed up and copied via share to the Server Cluster (step 150), as depicted in FIG. 1B. Backed up database may be restored to Database B, assuming Database A is currently in use by the Online WebServer (step 152). Feedback from Database A may be copied to Database B (step 154). Online WebServer user.config may be switched to database B (step 156). Database A can be dropped (step 158).

FIGS. 2-6 show different examples of how linkages can be performed at the WebServer, at the Front End of the system.

Figure 2:
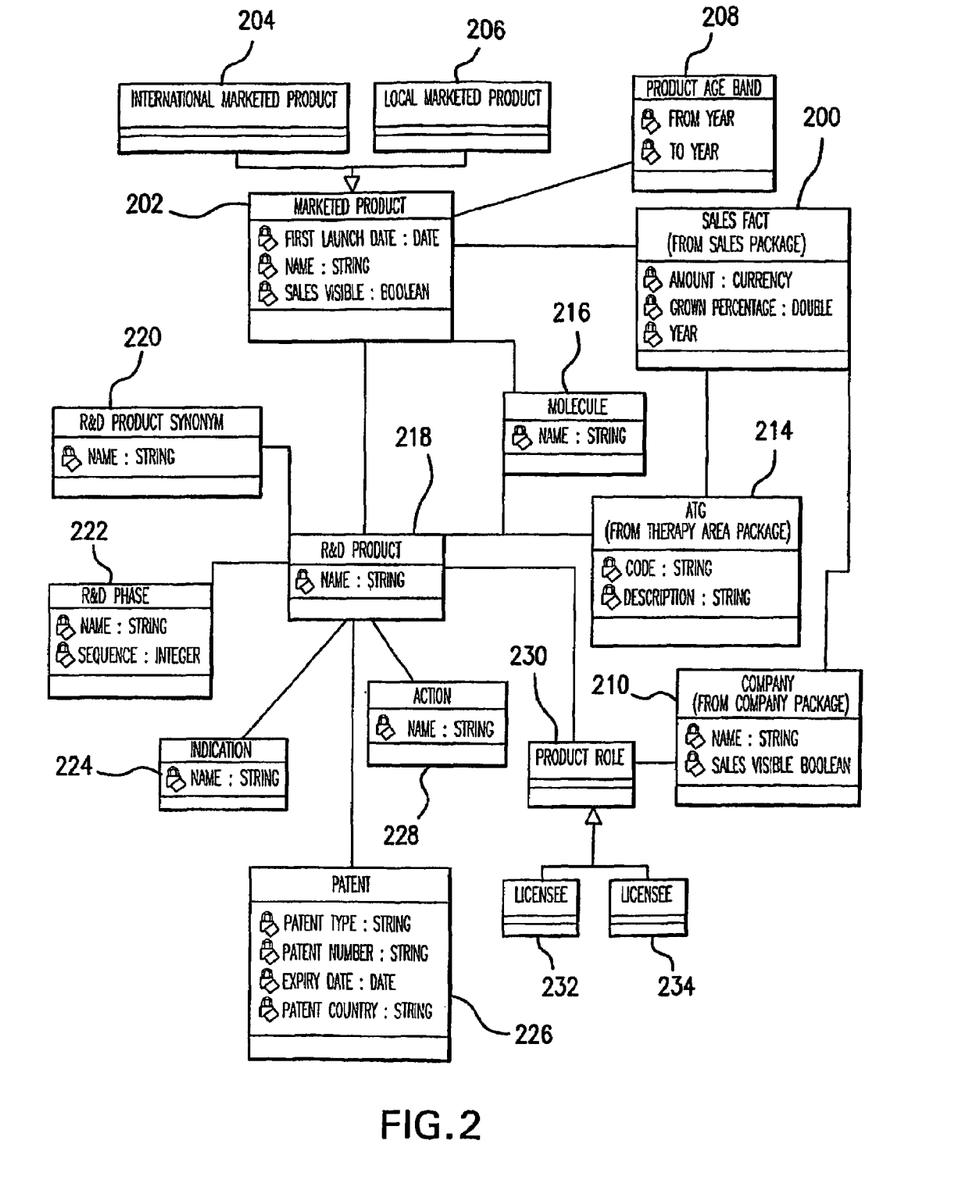
FIG. 2 is an illustrative diagram showing exemplary relationships for an item of data in accordance with the present invention.

Referring to FIG. 2, several exemplary relationships, which may be developed for a marketed product 202, are described.

Attributes such as the molecular makeup of a product used for marketing 216, the physical dollar sales of the product 210, the Anatomical Therapy Classification ("ATC") for the product 214 (a European classification), the companies which sell or distribute the product 212, research and development concerning the product 218, and the geographic distribution of the product 302 may each be inter-related to the product 202, as described below. Those skilled in the art should appreciate that such examples are not all inclusive, and that additional attributes may likewise be interrelated in accordance with the teachings herein.

FIG. 2 shows how a linkage is performed according to a first exemplary embodiment of the present invention. A marketed product 202 may be associated with a an international marketed product 204 and/or a local marketed product 206. The marketed product 202 may be associated with a product age band table 208. The marketed product may be associated with a sales fact table 210, based on information such as amount of sales, growth percentage, or year. The sales fact table 210 may provide a cumulative dollar total for sales during a predefined time period. The sales fact table may be associated with a company table. The sales fact table 210 may be associated with an ATC table 214, which may provide a cross-reference to the ATC group or groups which the marketed product resides. The marketed product 202 may be associated with a product molecule table 216. In order to associate the marketed product 202 to the product molecule table 216, the molecular composition of the marketed product may be examined. The product molecule table 216 may be associated with the ATC table 214. The marketed product may be associated with an research and development product table 218. The research and development product table may be associated with a research and development product synonym 220, which may provide a cross-reference of synonyms for various research and development products. The research and development product table 218 may be associated with a research and development phrase 222, which may indicate the last phase of development of the research and development product, e.g., animal testing, human testing, etc. The research and development product table 218 may be associated with an indication 224, which may contain a listing of disease that the various research and development products are used to treat. The research and development product table 218 may be associated with a patent 226, which may include the patent type, number, expiry date and/or patent country. The research and development product table 218 may be associated with an action 228, which may provide information relating to the use of the various research and development products with humans. The research and development product table 218 may be associated with a product role 230, which may be associated with the company 212. The product role may be associated with a licensee 232 and/or licensor 234.

Figure 3:
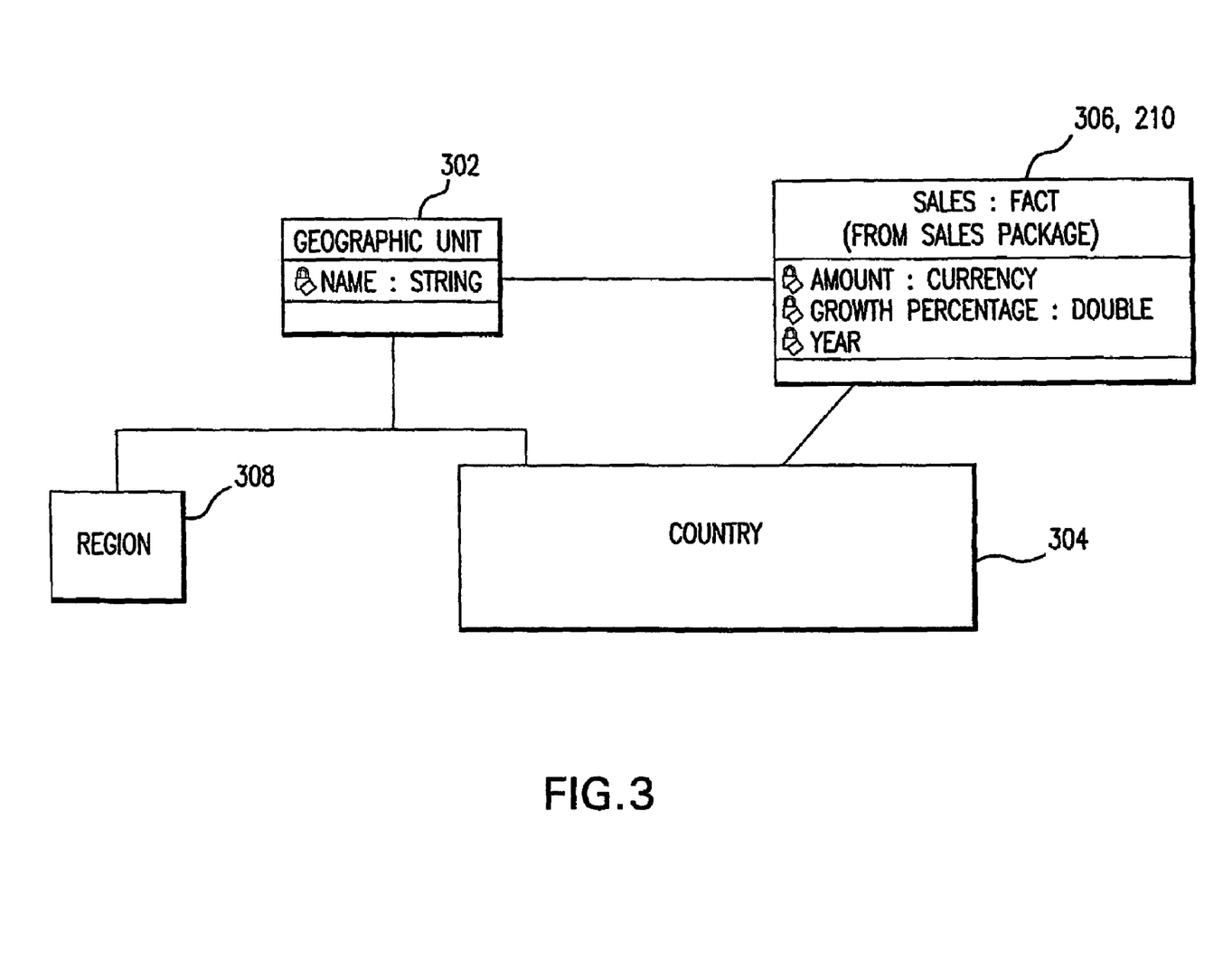
FIG. 3 is an illustrative diagram showing exemplary relationships for an item of data in accordance with the present invention.

FIG. 3 shows how a linkage is performed according to a second exemplary embodiment of the present invention. A geographic unit table 302 may be associated with a particular country table 304, which may provide a list of countries in which the marketed product 202 is marketed and distributed as well as may provide the relationships between countries, e.g., the European Union. The geographic unit table 302 may be associated with a particular sales fact table 306 based on information such as amount of sales, grown percentage or year. The geographic unit table 302 may be associated with a particular region table 308, which may provide regional geographic output.

Figure 4:
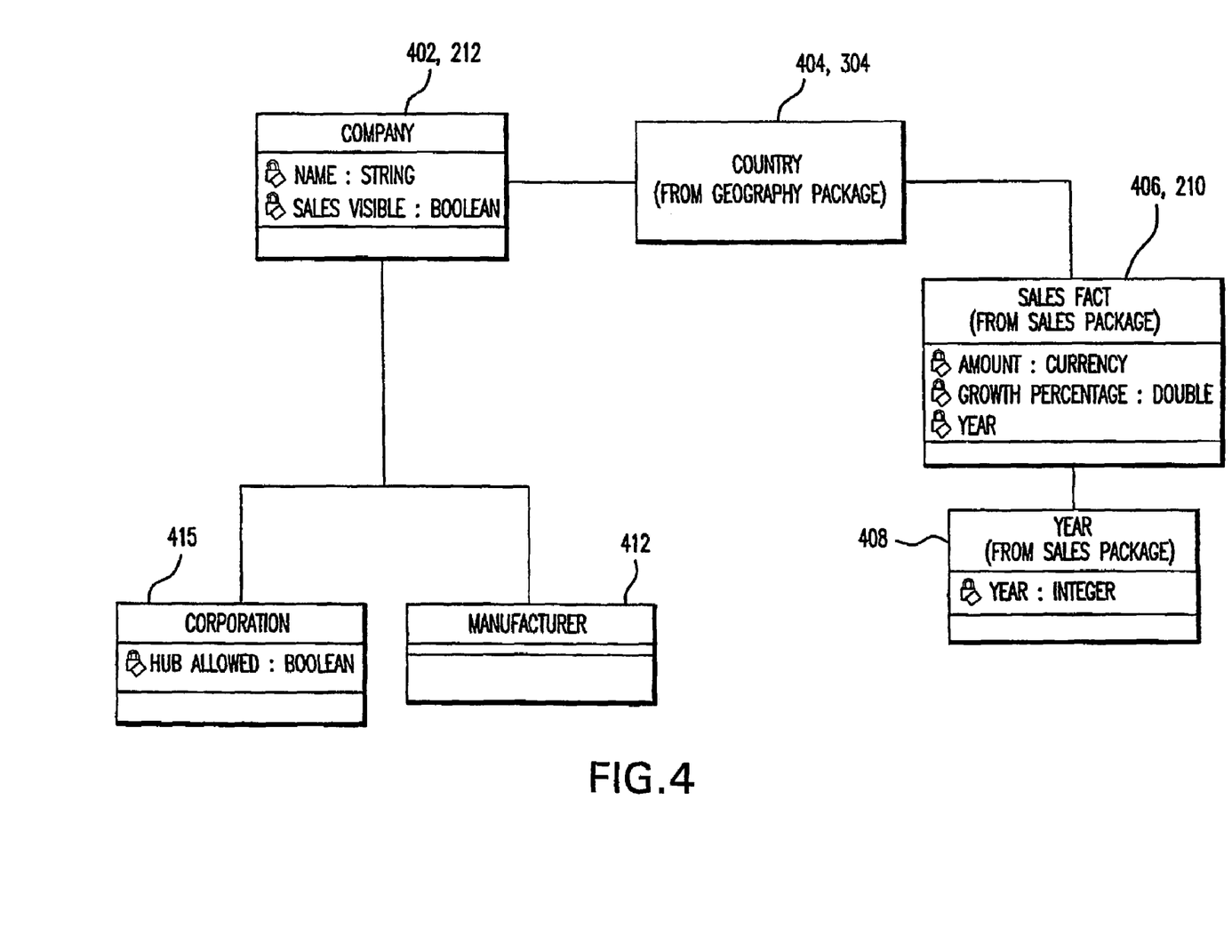
FIG. 4 is an illustrative diagram showing exemplary relationships for an item of data in accordance with the present invention.

FIG. 4 shows how a linkage is performed according to a third exemplary embodiment of the present invention. A company table 402, which may provide a listing of companies that sell or distribute the marketed product, may be associated with a particular country table 404, which may provide a listing of countries in which the company operates or is present. The country table 404 may be associated with a particular sales fact table 406 such as amount of sales, grown percentage or year 408. The company table 402 may be associated with a parent corporation 410. The company table may be associated with a particular manufacturer 412.

Figure 5:
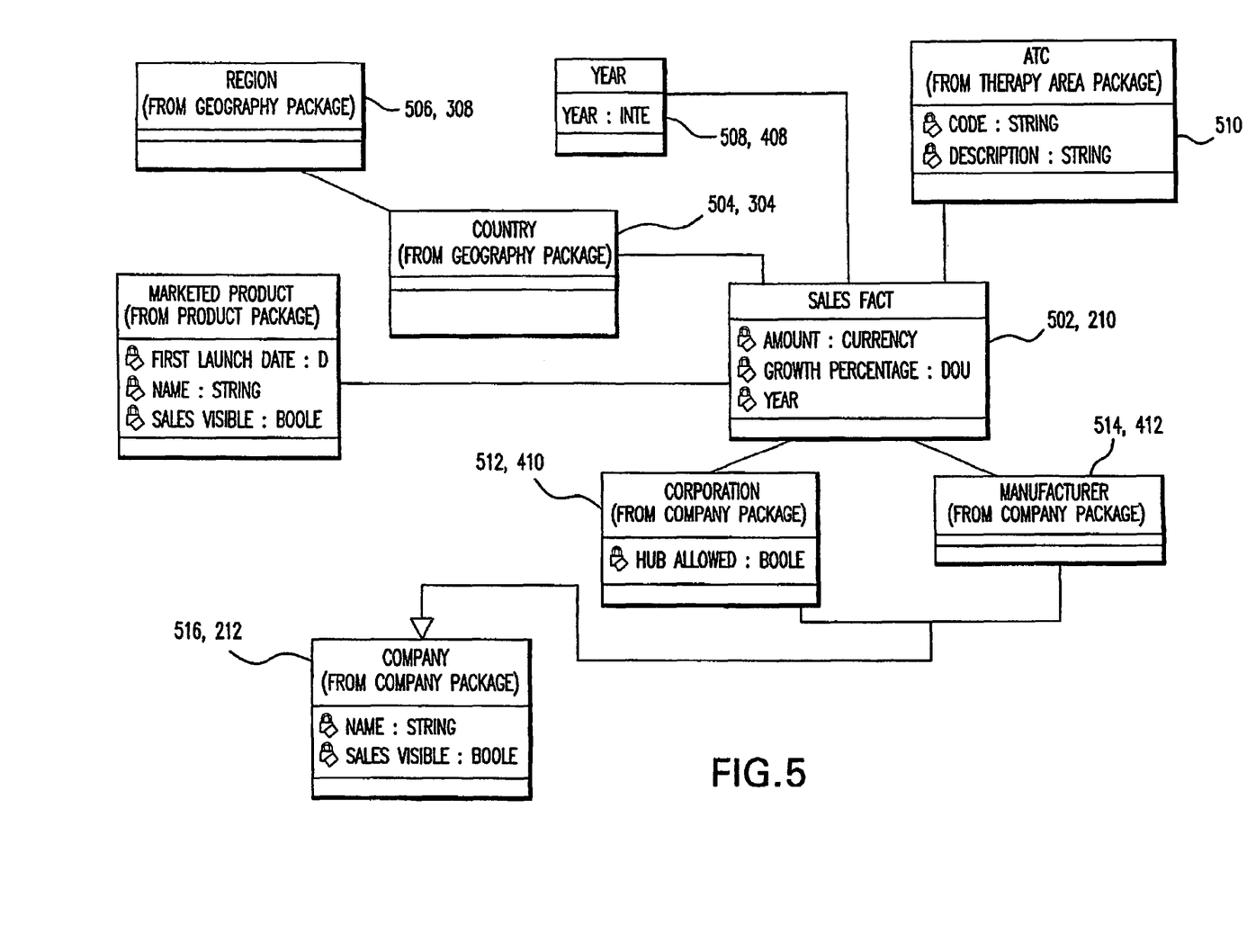
FIG. 5 is an illustrative diagram showing exemplary relationships for an item of data in accordance with the present invention.

FIG. 5 shows how a linkage is performed according to a fourth exemplary embodiment of the present invention. A sales fact table 502 may be associated with a particular country table 504. The country table 504 may be associated with a particular region 506. The sales fact table 502 may be associated with a particular year 508. The sales fact table 502 may be associated with an ATC table 510. The sales fact table 502 may be associated with a parent corporation. The sales fact table 502 may be associated with a particular manufacturer 514. The manufacturer 514 and/or parent corporation 512 may be associated with a particular company 516.

Figure 6:
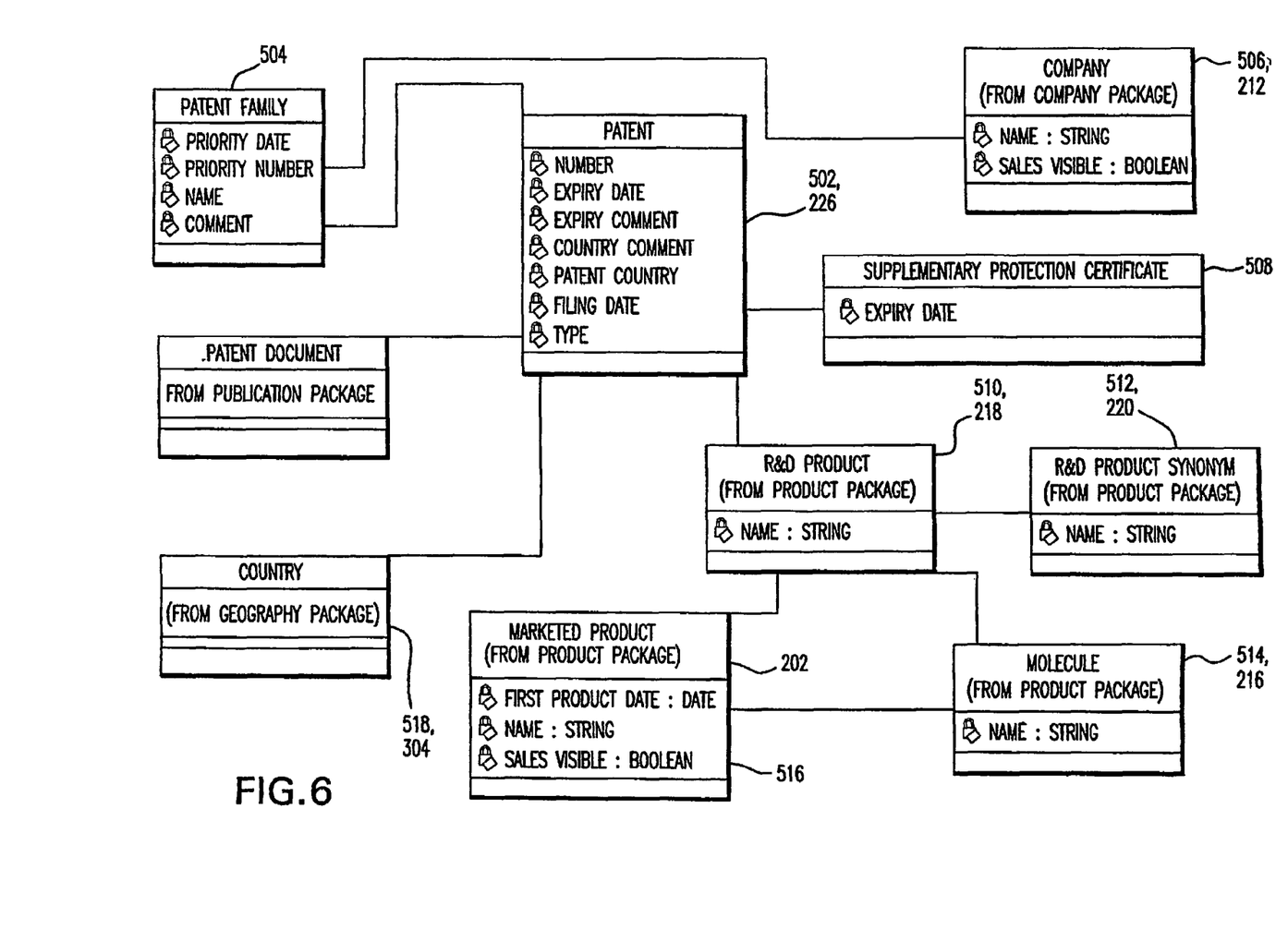
FIG. 6 is an illustrative diagram showing exemplary relationships for an item of data in accordance with the present invention.

FIG. 6 shows how a linkage is performed according to a fifth exemplary embodiment of the present invention. A patent 502 may be associated with a patent family table 504. The patent family table 504 may include a priority date, a priority number, a name, and a comment. The patent family table 504 may be associated with a company 506. The patent 502 may be associated with a supplementary protection certificate 508, which may have an expiry date. The patent 502 may be associated with an research and development product table 510. The research and development product table 510 may be associated with a research and development product synonym 512. The research and development product table 510 may be associated with a Molecule table 514. The research and development product table 510 may be associated with a marketed product 516. The patent 502 may be associated with a particular country 518.

Figure 7:
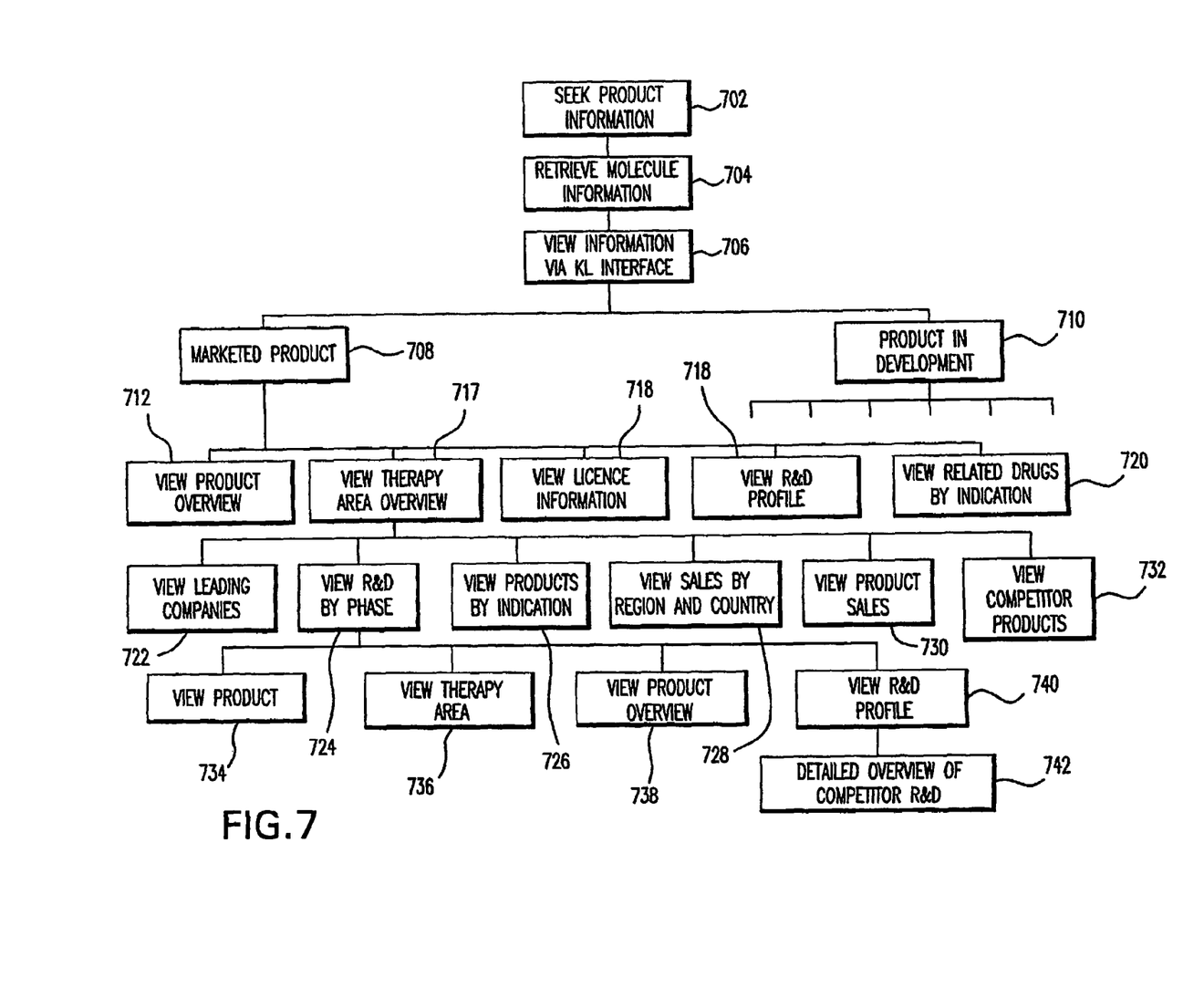
FIG. 7 is an illustrative diagram showing exemplary relationships for an item of data in accordance with the present invention.
Figure 8:
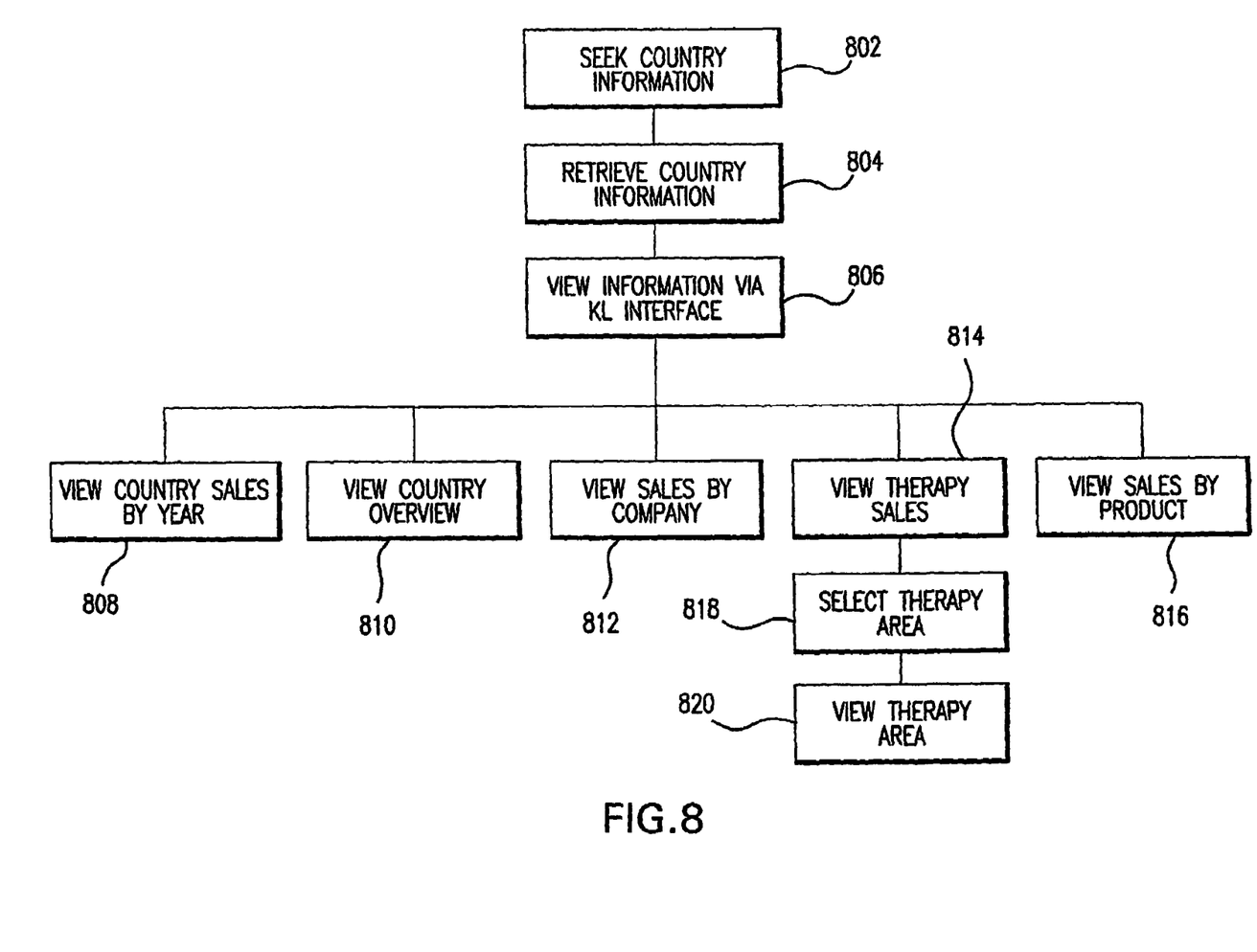
FIG. 8 is an illustrative diagram showing exemplary relationships for an item of data in accordance with the present invention.
Figure 9:
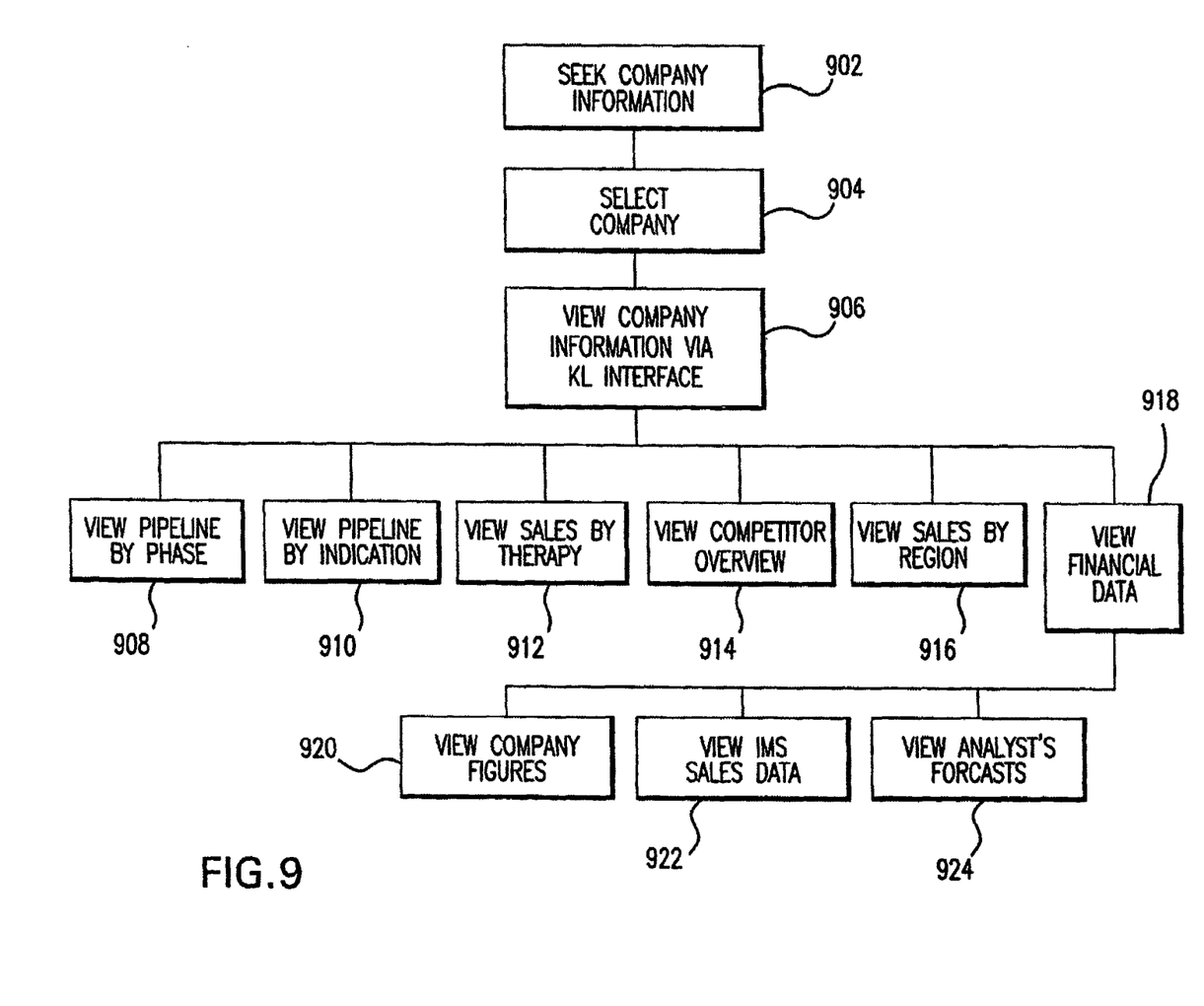
FIG. 9 is an illustrative diagram showing exemplary relationships for an item of data in accordance with the present invention.

FIGS. 7-9 show different examples of how a user may search for information, using the Back End of the system. This assumes a populated and linked database is already in existence.

FIG. 7 shows how a user performs a search seeking product information according to a sixth exemplary embodiment of the present invention. A user seeks product information 702, then a search tool of the system may perform the searching. The system may retrieve molecule information 704. This may be viewed via a KL interface 706. This information may include marketed products 708 and products in development 710. If a user seeks more information on the marketed product 708, a user may view product overview 712, therapy area overview 714, license information 716, research and development profile 718, and/or related drugs by indication 720. If a user seeks more information on the therapy area overview 714, for example, a user may view leading companies 722, research and development by Phase 724, Products by indication 726, sales by region and country 728, product sales 730, and/or competitor products 732. If a user seeks more information on the research and development phase 724, for example, a user may view product 734, therapy area 736, product overview 738, and/or research and development profile 740. If a user seeks more information on the research and development profile 740, for example, a user may view a detailed overview of competitor research and development 742.

FIG. 8 shows how a user performs a search seeking country information according to a sixth exemplary embodiment of the present invention. A user seeks country information 802, then a search tool of the system may perform the searching. The system may retrieve country information 804. This may be viewed via a KL interface 806. This information may include country sales by year 808, country overview 810, sales by company 812, therapy sales 814, and sales by product 816. If a user seeks more information on the therapy sales 818, for example, a user may select a therapy area 818. If a user seeks more information on the therapy area 818, for example, a user may view the therapy area 820.

FIG. 9 shows how a user performs a search seeking country information according to a seventh exemplary embodiment of the present invention. A user seeks company information 902, then a search tool of the system may perform the searching. The system may retrieve company information after a company is selected 904. This may be viewed via a KL interface 906. This information may include pipeline by phase 908, pipeline by indication 910, sales by therapy 912, competitor overview 914, sales by region 916, and financial data 918. If a user seeks more information on financial data 918, for example, a user may view company figures 920, IMS sales data 922, and/or analyst's forecasts 924.

Figure 10:
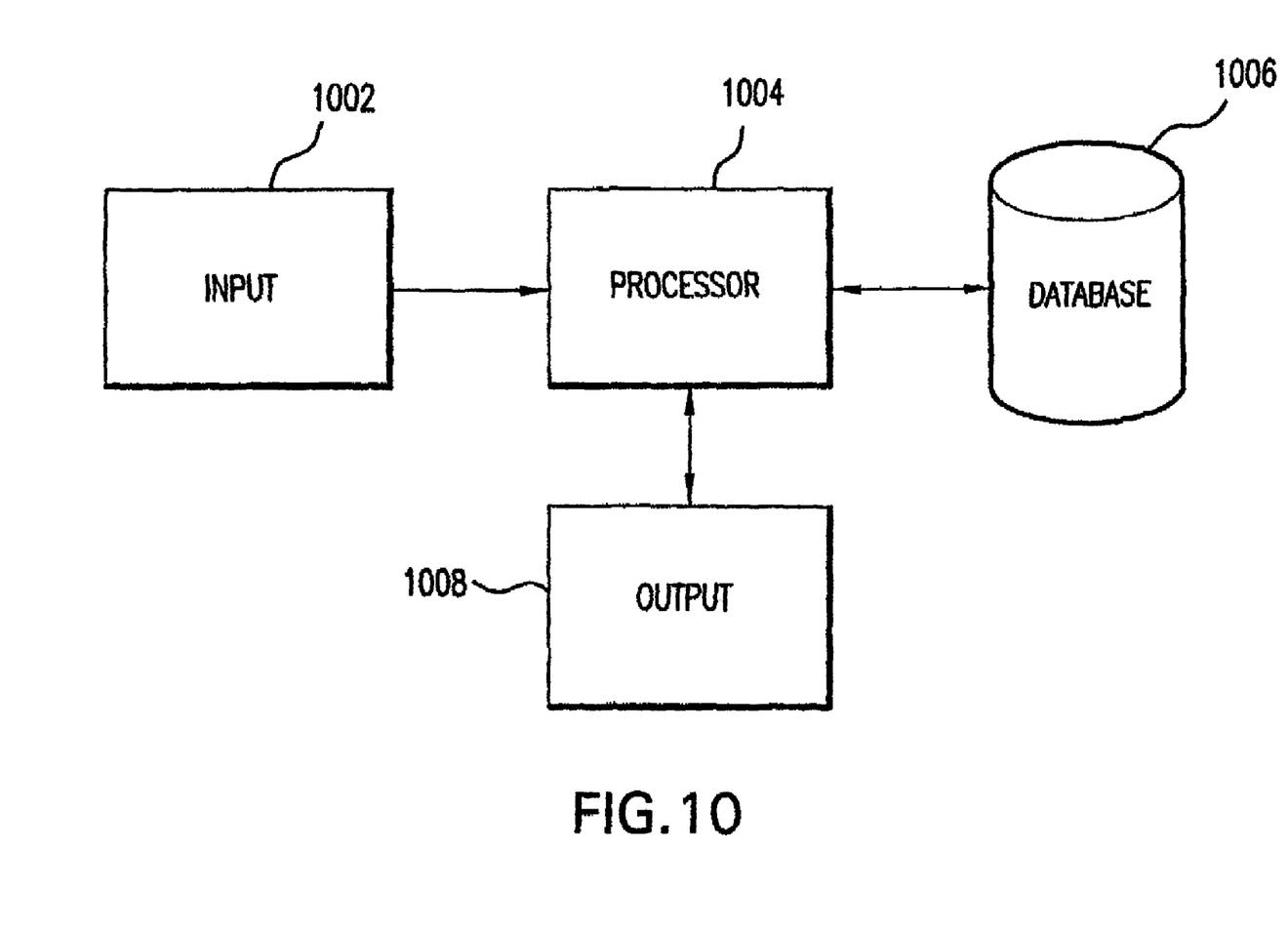
FIG. 10 is a block diagram of an exemplary system in accordance with the present invention.

Referring next to FIG. 10, information concerning each of these attributes may be supplied or derived from numerous different data sources, and stored in one or more databases 1006 via one or more input devices 1002, such a CD-ROM drive. Database 1006 may be a relational database residing on a network computer, or may also be a mainframe computer. Processor 1004 manages the storage of data, requests for information received at input 1002, and data output 1008. Processor 1004 may embody a computer network server or web-enabled server. Output 1008 may be any human readable output, but preferably is a plurality of computer network clients capable of receiving data from a web-enabled server.

Figure 11:
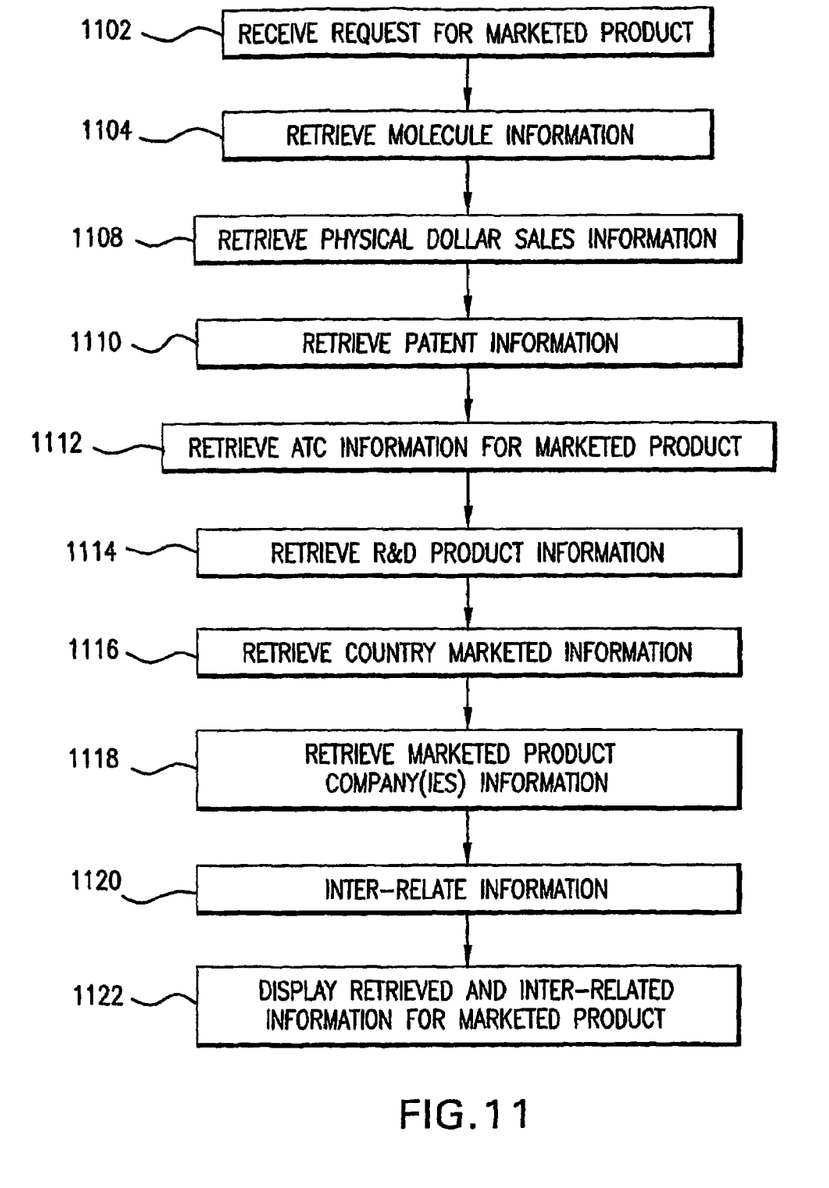
FIG. 11 is a flow diagram of an exemplary method in accordance with the present invention.

A preferred methodology in accordance with the present invention is described with reference to FIG. 11. In operation, a request for data for a marketed product is received in step 1102. The request may be made, e.g., by a human user via input 1002, which may be a mouse or keyboard device.

Depending on the request, molecule information, publication information, physical dollar sales information, patent information, ATC information, research and development information, geographic information, and/or distribution company information may be retrieved in steps 1104-1118. The retrieved information is then inter-related 1120 by keying in on at least one common field, e.g., marketed product 202, in step 1120, and displayed to a user in step 1122.

The above system and method may be implemented by many computer languages commonly known in the art and may operate on many computer platforms which include both volatile and non-volatile memory storage devices. In a preferred embodiment, the system and method of the present invention is implemented, in whole or in part, on a mainframe, or UNIX based system using Oracle, SQL, and C#. Software code encapsulating the functionality of the present inventive technique may be implemented on such computer systems, preferably written in Oracle PL*SQL, C, C++, or any other commonly known programming language.

Although the invention has been described herein by reference to an exemplary embodiment thereof, it will be understood that such embodiment is susceptible of modification and variation without departing from the inventive concepts disclosed. For example, a company's name could be queried, where the present system and method would output all marketed products of that company and all other related technical information of the marketed products returned. All such modifications and variations, therefore, are intended to be encompassed within the spirit and scope of the appended claims.

We claim:

1. A system for inter-relating two or more product attributes to a marketed pharmaceutical product, derived from separate data source with dissimilar data, comprising: (a) a database storing product attribute information for two or more attributes derived from separate data source with dissimilar data that relate to said marketed pharmaceutical product; (b) an input device, coupled to said database, for receiving a request for product attribute information concerning said marketed pharmaceutical product; and (c) a processor, coupled to said database and to said input device, for inter-relating one or more product attribute information items from said database to said marketed pharmaceutical product in accordance with said request.

2. The system of claim 1, further comprising an output, coupled to said processor, for providing said one or more inter-related product attribute information items in a human readable format.

3. The system of claim 2, wherein said output comprises a client computer.

4. The system of claim 1, wherein said product attribute information includes marketed product molecule data.

5. The system of claim 1, wherein said product attribute information includes information relating to publications discussing said marketed pharmaceutical product.

6. The system of claim 1, wherein said product attribute information includes physical dollar sales data for said marketed pharmaceutical product.

7. The system of claim 1, wherein said product attribute information includes marketed pharmaceutical product relationship data.

8. The system of claim 1, wherein said product attribute information includes marketed pharmaceutical product anatomical therapy classification data.

9. The system of claim 1, wherein said product attribute information includes marketed pharmaceutical product related research and development product data.

10. The system of claim 1, wherein said product attribute information includes country marketed data for said marketed pharmaceutical product.

11. The system of claim 1, wherein said product attribute information includes marketed pharmaceutical product companies data.

12. A method for inter-relating two or more product attributes to a marketed pharmaceutical product derived from separate data source with dissimilar data, comprising the steps of: (a) storing product attribute information for two or more attributes that relate to said marketed pharmaceutical product derived from separate data source with dissimilar data; (b) receiving a request for product attribute information concerning said marketed pharmaceutical product; and (c) inter-relating one or more product attribute information items from said stored product attribute information to said marketed pharmaceutical product in accordance with said request.

13. The method of claim 12, further comprising the step of displaying said inter-related product attribute information.

14. The method of claim 12, wherein said step of inter-relating said product attribute information items includes inter-relating marketed product molecule data.

15. The method of claim 12, wherein said step of inter-relating said product attribute information items includes inter-relating information relating to publications discussing said marketed pharmaceutical product.

16. The method of claim 12, wherein said step of inter-relating said product attribute information items includes inter-relating physical dollar sales data for said marketed pharmaceutical product.

17. The method of claim 12, wherein said step of inter-relating said product attribute information items includes inter-relating marketed pharmaceutical product relationship data.

18. The method of claim 12, wherein said step of inter-relating said product attribute information items includes inter-relating marketed pharmaceutical product anatomical therapy classification data.

19. The method of claim 12, wherein said step of inter-relating said product attribute information items includes inter-relating marketed pharmaceutical product related research and development product data.

20. The method of claim 12, wherein said step of inter-relating said product attribute information items includes inter-relating country marketed data for said marketed pharmaceutical product.

21. The method of claim 12, wherein said step of inter-relating said product attribute information items includes inter-relating marketed pharmaceutical product companies data.

* * * * *